(12) United States Patent
Kiilerich

(10) Patent No.: US 9,144,647 B2
(45) Date of Patent: Sep. 29, 2015

(54) MAGNETIC TIME DELAY INDICATOR AND AN INJECTION DEVICE INCORPORATING SUCH

(71) Applicant: Novo Nordisk A/S, Bagsvaerd (DK)

(72) Inventor: Ebbe Kiilerich, Copenhagen NV (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/357,948

(22) PCT Filed: Nov. 15, 2012

(86) PCT No.: PCT/EP2012/072719
§ 371 (c)(1),
(2) Date: May 13, 2014

(87) PCT Pub. No.: WO2013/072412
PCT Pub. Date: May 23, 2013

(65) Prior Publication Data
US 2014/0330212 A1  Nov. 6, 2014

Related U.S. Application Data

(60) Provisional application No. 61/562,084, filed on Nov. 21, 2011.

(30) Foreign Application Priority Data

Nov. 15, 2011 (EP) .................................... 11189131

(51) Int. Cl.
*G04F 1/06* (2006.01)
*A61M 5/20* (2006.01)
(Continued)

(52) U.S. Cl.
CPC ................ *A61M 5/20* (2013.01); *A61J 7/0409* (2013.01); *G04F 1/066* (2013.01); *G04F 13/06* (2013.01);
(Continued)

(58) Field of Classification Search
CPC ............. G04F 1/00; G04F 1/06; G04F 1/005; G04F 1/066; B65D 85/40
USPC ....................................... 368/93–95
See application file for complete search history.

(56) References Cited

U.S. PATENT DOCUMENTS 2,555,513 A   6/1951 Schweitzer, Jr.
2,868,923 A * 1/1959 Epstein .......................... 335/63
(Continued)

FOREIGN PATENT DOCUMENTS

WO        9730742        8/1997
WO    2004/010231 A2    1/2004

OTHER PUBLICATIONS

FarmerJohn,Our Glass, Ferrofluid TimePiece, Apr. 28, 2003; http://www.halfbakery.com/idea/Our_20Glass_2c_20Ferrofluid_20Timepiece; OTH.
(Continued)

*Primary Examiner* — Sean Kayes
(74) *Attorney, Agent, or Firm* — Wesley Nicolas

(57) ABSTRACT

The present invention relates to a time delay indicator (1) for an injection device for administering a drug into the body of a subject user wherein the time delay indicator is configured for indicating after administration that a dose of the drug actually has been administered and for maintaining this indication until lapse of a pre-determined time interval. The time delay indicator is based on a magnetic liquid (6) being physically moved by a magnet (10).

11 Claims, 3 Drawing Sheets

(51) Int. Cl.
  *A61J 7/04* (2006.01)
  *G04F 13/06* (2006.01)
  *H01H 36/00* (2006.01)
  *A61M 5/178* (2006.01)

(52) U.S. Cl.
  CPC ............... *H01H 36/00* (2013.01); *A61J 1/1418* (2015.05); *A61J 7/0418* (2015.05); *A61J 7/0427* (2015.05); *A61J 7/0436* (2015.05); *A61J 7/0472* (2013.01); *A61J 2007/0427* (2013.01); *A61M 5/178* (2013.01); *A61M 2005/2026* (2013.01); *A61M 2205/507* (2013.01); *A61M 2205/583* (2013.01); *G04F 1/06* (2013.01)

(56) References Cited

U.S. PATENT DOCUMENTS

| | | | | |
|---|---|---|---|---|
| 3,915,340 A | * | 10/1975 | Koeleman | 222/23 |
| 3,951,309 A | * | 4/1976 | Kadowaki | 222/64 |
| 4,474,481 A | * | 10/1984 | Croyle | 368/93 |
| 4,959,819 A | * | 9/1990 | Haczewski, Jr. | 368/93 |
| 5,457,665 A | * | 10/1995 | Reid | 368/93 |
| 5,717,283 A | | 2/1998 | Biegelsen et al. | |
| 5,810,640 A | | 9/1998 | Clarke et al. | |
| 2011/0208125 A1 | | 8/2011 | Larsen et al. | |

OTHER PUBLICATIONS

H Crew ∧ A De Salvio,Dialogues Concerning Two New Sciences,; http://www.new-science-theory.com/galileo-galilei.php; OTH.

Hour Glass Cartoon 5—Search ID BRON2048,; http://www.cartoonstock.com/directory/h/hour_glass.asp; OTH.

Kenny, Electromagnet Project, Sep. 4, 2010,; http://www.physicsforums.com/showthread_php?t=426409; OTH.

* cited by examiner

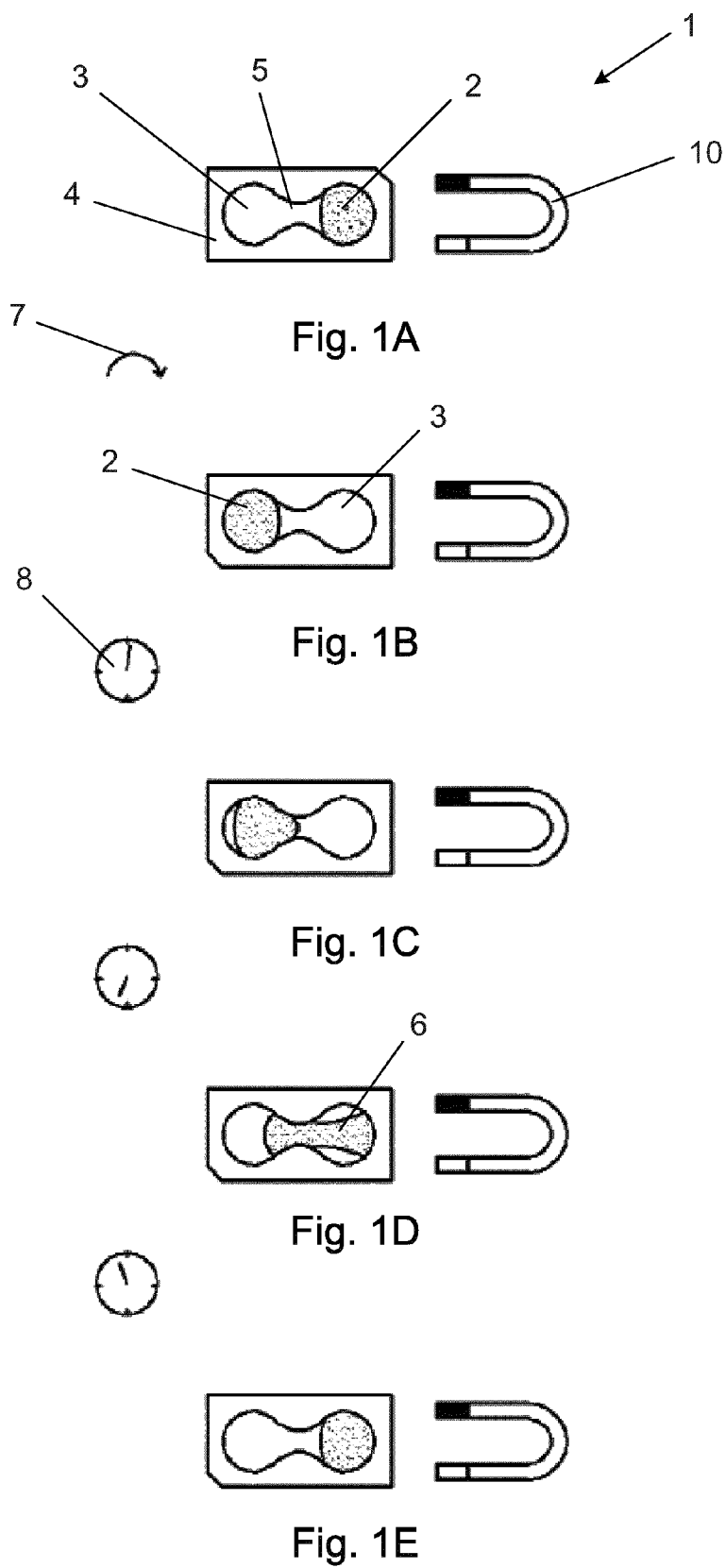

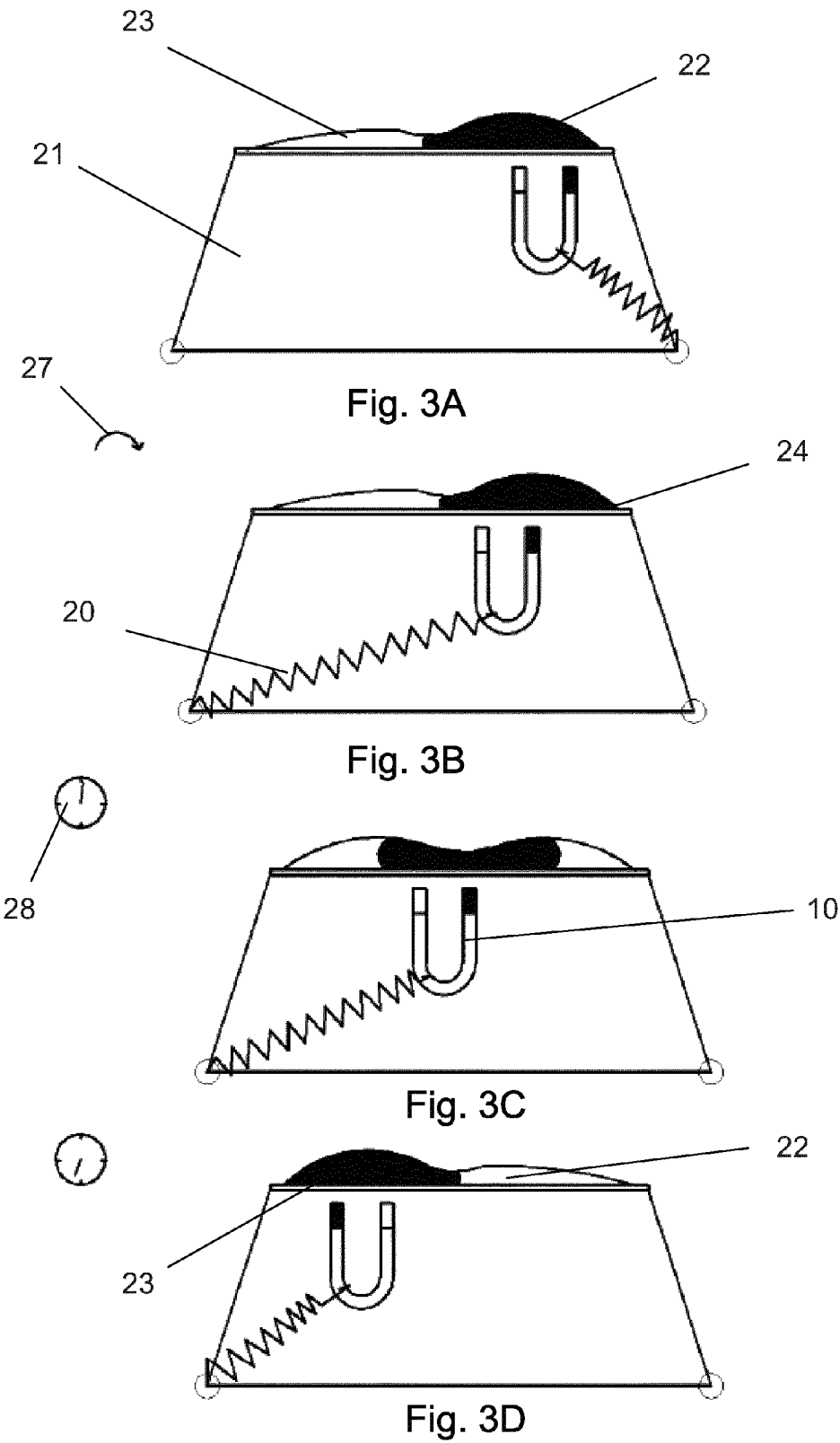

MAGNETIC TIME DELAY INDICATOR AND AN INJECTION DEVICE INCORPORATING SUCH

CROSS-REFERENCE TO RELATED APPLICATIONS

This application is a 35 U.S.C. §371 National Stage application of International Application PCT/EP2012/072719 (published as WO 2013/072412), filed Nov. 15, 2012, which claimed priority of European Patent Application 11189131.3, filed Nov. 15, 2011; this application claims priority under 35 U.S.C. §119 of U.S. Provisional Application 61/562,084; filed Nov. 21, 2011.

THE TECHNICAL FIELD OF THE INVENTION

The present invention relates to a time delay indicator for use with medical injection devices for administering a drug into the body of a user wherein the indicator is configured for visually indicating after administration of a dose of drug that a predetermined time interval has lapsed. Further, the present invention relates to an injection device incorporating such time delay indicator.

DESCRIPTION OF RELATED ART

People suffering from diabetes have to inject themselves with insulin at a daily basis. For this purpose a great number of different pen systems have been developed over the last 30 years. The typical diabetes patient will require injections of insulin several times during the course of a week or a day. However, typical injection devices do not address the problem of a user not remembering when the last injection was administered.

Even shortly after administering a dose of insulin, the user now and then will be in doubt as to whether he or she actually carried out an injection or not. This doubt could occur minutes or even hours after the injection had been performed. Thus, there exist the potential hazard that the user chooses not to take his medication, or that he takes it twice.

WO 97/30742 discloses an electronic injection device provided with an electronic monitoring system adapted to automatically start an electronic timer when the selected dose is injected and to show the progress in time on an electronic display. Such an injection device generally provides a satisfactory solution to the problem addressed above. However, for simpler injection devices such as disposable injection devices i.e. injection devices which are prefilled with a predetermined amount of liquid drug and discarded after use, the solution with integrated electronics will in most cases not be economically viable. In addition, such a solution may not be environmentally acceptable due to the potential increase in the disposal of electronic components such as batteries etc.

A different solution is disclosed in WO 2004/010231. Here an electronic timer in the cap of an injection device generates a first time stamp once the cap is removed and a second time stamp once the cap is attached to the injection device. If the cap has been removed for a certain time interval, the electronic control assumes that an injection has been performed and starts an electronic timer. This solution is suitable for prefilled injection device since the cap can be moved onto the next subsequent prefilled injection device the user needs in his treatment. Thus, the prefilled injection device can be discarded but the electronic timer in the cap can be reused.

A purely mechanical time delay indicator which can be integrated into a prefilled injection device is disclosed in US 2011/0208125.

Hourglasses also known as egg timers are widely known for indicating that a predetermined time interval has lapsed. Such time delay indicators usually comprise two chambers connected by a narrow channel or orifice through which sand (or liquid) moves from one chamber to the other chamber. The composition of the sand contained in the chambers and the diameter of the orifice or the channel is decisive for the time interval it takes the gravity of the earth to move the sand from one chamber to the other chamber. In such egg timers the two chambers needs to be provided above and below each other in order for the gravity to shift the sand from the upper chamber to the lower chamber.

An electrical switch having a magnetic time delay mechanism is disclosed in U.S. Pat. No. 2,555,513. Here a flowable magnetic material is provided in an upper chamber and moved by gravity through a narrow orifice and into a lower chamber. Once a sufficient amount of the magnetic material is present in the lower chamber the summarized magnetic force of this magnetic material has grown large enough to pull the trigger of a switch. The mechanism is further provided with a handle such that a user can shift the positions between the upper and the lower chamber to start a new cycle. However, in this magnetic time delay mechanism, the flowable magnetic material is shifted due to the gravity, thus requiring the two chambers to be physically located above and below each other.

Further, a magnetic toy comprising a liquid magnetic gel which can be pulled through an opening by a magnetic force delivered by a permanent magnet is disclosed in U.S. Pat. No. 5,810,640.

DESCRIPTION OF THE INVENTION

Having regard to the above identified prior art, it is an object of the present invention to provide a time delay indicator which provides a visual indication output for signalling to a user that a predetermined time interval has lapsed, the timer being of less complex construction compared to prior art solutions. A further object is to provide a simple and cost-effective time delay indicator suitable for inclusion as an integral part of a disposable injection device and which enables easier operation of the injection device. Yet, a further object is to provide a time delay indicator which does not depend on mechanical means, but rather operates purely on magnetism.

The invention is defined in claim 1.

In a first aspect the present invention relates to a time delay indicator comprising two different compartments connected by a narrow channel or orifice e.g. like an hourglass.

One of the two compartments holds a flowable magnetic liquid which can flow from one compartment to the other compartment through the narrow channel. In an ordinary hourglass as an egg-timer the influence of the gravity force of the earth typically moves sand from one chamber to a second chamber thus one chamber is located above the other chamber such that gravity can shift the sand from the upper chamber to the lower chamber. In the present invention, the gravity of the earth has been substituted by a magnet, such that the content of the compartments are moved purely by the magnetic force of the magnet, thus the two chambers can be orientated next to each other and not necessarily above each other.

The chamber not containing the flowable magnetic liquid can be empty or it can be filled with another non-magnetic liquid which is then moved to the first chamber as the magnetic liquid moves into the second chamber. Such non-magnetic liquid would preferably have a density as the magnetic liquid. Having such non-magnetic liquid to gradually supersede the magnetic liquid as it flow into the other chamber would fully make the system immune to the gravity as the full volume of the two chambers and the channel would constantly be filled by the two different liquids.

In one example the magnetic liquid is moved away from the magnet by moving the compartment containing the magnetic liquid away from the magnet. This can be done very much like in an ordinary hourglass where the hourglass is swung over an axis perpendicular to the channel connecting the two compartments.

In another example the magnetic liquid is moved to the other compartment by forcing it through the narrow channel, where after the magnet pulls the magnetic liquid back into the compartment. After a predetermined time interval, the magnetic liquid is thus returned to the first compartment.

In an alternative embodiment the magnetic liquid follows the movement of the magnetic means which magnetic means could in one embodiment be moved by a spring. During dosing, the spring could be tightened where after the tighten spring during its retraction to its untighten position pulls the magnet and thereby the magnetic liquid.

The magnetic force of the magnet and the opening of the orifice together with the composition of the magnetic liquid are decisive for the time it takes the magnetic liquid to move from one compartment to the other compartment. As the magnetic liquid moves, the visual appearance of the compartments changes continuously and once the magnetic liquid has fully moved from one compartment to the other compartment, the user can easy identify that the predetermined time interval has lapsed.

The magnet is preferable a permanent magnet to keep the time delay indicator as simple as possible but in more complex settings any kind of electro magnet could be used.

In a further aspect of the invention, the time delay indicator is built into a disposable injection device such that a user activates the time delay indicator once he presses an injection button to perform an injection.

DEFINITIONS

A "magnetic liquid" is a liquid solution (including a gel) which contain magnetic particles such that the liquid can be moved by the influence of a magnet. Such liquids, which become magnetized in the presence of a magnetic field are often referred to as "Ferrofluids" since the normally contain ferromagnetic particles suspended in a carrier fluid. A number of such magnetic liquids or gels are referred to in U.S. Pat. No. 5,810,640.

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container containing the drug. Cartridges are usually made from glass but could also be moulded from any suitable polymer. A cartridge or ampoule is preferably sealed at one end by a pierceable membrane which can be pierced e.g. by the non-patient end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 1A-E show a magnetic time delay indicator.

FIG. 3A-D show another embodiment of a magnetic time delay indicator.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Figure 2A:
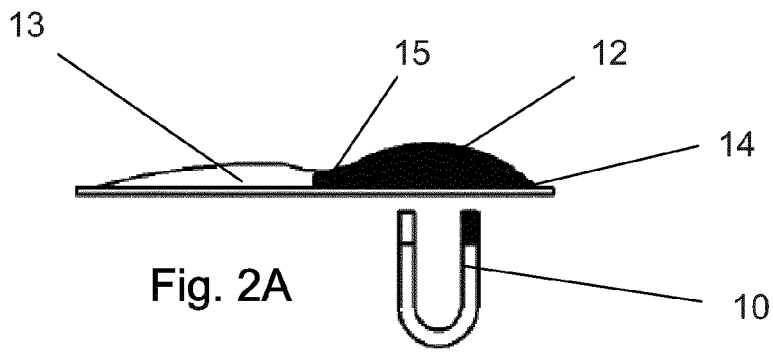
FIG. 2A-E show a different embodiment of a magnetic time delay indicator.

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

FIG. 1A-E discloses a magnetic time delay arrangement 1. The time delay arrangement 1 comprises a first compartment 2 and a second compartment 3 situated in a housing 4 and connected to each other through an orifice 5. In FIG. 1A, prior to performing an injection, a magnetic liquid 6 is present in the first compartment 2 only. After (or during) having performed an injection, the first compartment 2 is moved away from the permanent magnet 10 as disclosed in FIG. 1B e.g. by rotating the housing 4 containing the two compartments 2, 3 as indicated by the arrow 7.

In one embodiment, the second compartment 3 can instead of being empty be filed with a non-magnetic liquid which would then be forced into the first compartment 2 as the magnetic liquid 6 moves into second compartment 3 thereby superseding the magnetic liquid 6 in the first compartment.

As time passes as indicated on the analogue watch 8 the magnetic liquid 6 is pulled through the orifice 5 and into the second chamber 3 by the permanent magnet 10 as indicated in FIGS. 1C and 1D.

After a predetermined time interval all the magnetic liquid 6 will be present in the second compartment 3 only, as disclosed in FIG. 1E.

If the predetermined time interval for moving the magnetic liquid 6 through the orifice 5 is e.g. set for one hour, then the user can in the time interval from the injection is performed and until one hour has passed observe the magnetic liquid 6 move from the first compartment 2 and into the second compartment 3. When more than one hour has passed, all the magnetic liquid 6 will be present in the second compartment 3, thereby informing the user that more than one hour has passed since the last injection was performed.

An alternative solution is disclosed in FIG. 2A-E. Here the magnetic liquid 16 is encapsulated in a bag-like structure 14 divided into a first compartment 12 and a second compartment 13. These two compartments 12, 13 is connected to each other through an opening or orifice 15.

Prior to the injection all the magnetic liquid 16 is present in the first compartment 12 as disclosed in FIG. 2A.

Figure 2B:
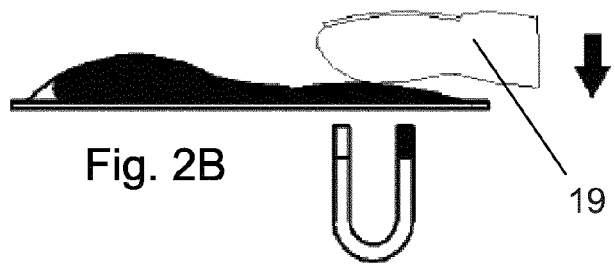

During injection, the user exerts a pressure on the first compartment 12 e.g. by pressing a finger 19 on the first compartment 12. The pressure moves the magnetic liquid 16 into the second chamber 13 as illustrated in FIG. 2B.

Figure 2C:
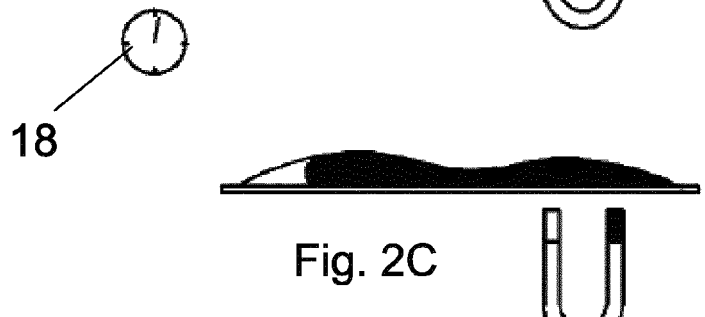
Figure 2D:
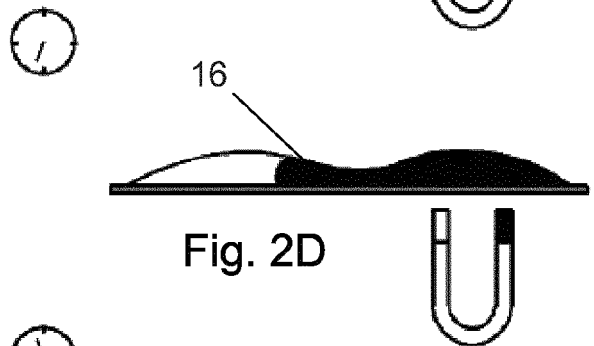

When the finger 19 is removed and no pressure exist, the magnetic liquid 16 will start to flow back to the first compartment 12 due to the magnetic force from the permanent magnet 10 as disclosed in FIG. 2C.

Figure 2E:
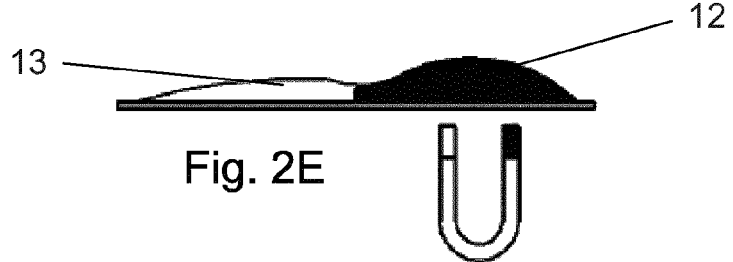

The analogue watch 18 illustrates the passing of time. In this example all the magnetic liquid 16 will be back in the first compartment 12 one hour after the pressure from the finger 19 has been released as illustrated in FIG. 2E.

A user viewing the bag-like structure 14 will visible observe that e.g. within the first hour passing since the last injection has been performed magnetic liquid 16 is present in the second compartment 13 where after the second compartment 13 is left empty.

Yet a different alternative is disclosed in FIG. 3A-D. Here the magnetic liquid 26 is also present in a bag-like structure 24 and movable from the first chamber 22 through a neck 25 and into the second chamber 23. The bag-like structure 24 is permanent fixed and the permanent magnet 10 is secured in a rotatable housing 21 by a spring 20.

The permanent magnet 10 will be magnetically adhered to the magnetic liquid 26 such that the magnetic liquid 26 will follow the permanent magnet 10 and vice versa.

Once the injection has been performed or even during the injection, the housing 21 is rotated as indicated with the arrow 27 in FIG. 3B. This rotation tightens the spring 20 which immediately starts to pull the permanent magnet 10 toward the released position of the spring 10 as depictured in FIG. 3C.

The characteristic of the spring 10 could e.g. be such that the spring 10 has returned to its original shape within half an hour as indicated by the watch 28. As a result of this, the magnetic liquid 26 is drawn into the second chamber 23 by the permanent magnet 10 as disclosed in FIGS. 3C and 3D. After half an hour all the magnetic liquid 26 will be moved from the first chamber 22 and into the second chamber 23.

A user viewing e.g. the second chamber 23 will visible see an empty second chamber 23 if no injection has been performed as in FIG. 3A. The first half hour passing after an injection has been performed, the user will see the second chamber 23 gradually becoming flooded with the magnetic liquid 26 as in FIG. 3C and after half an hour has passed, the second chamber 23 will be completely flooded as indicated in FIG. 3D.

Some preferred embodiments have been shown in the foregoing, but it should be stressed that the invention is not limited to these, but may be embodied in other ways within the subject matter defined in the following claims.

The invention claimed is:

1. A magnetic time delay indicator providing a visual output for signalling to a user that a predetermined time interval has lapsed, comprising:
   a first compartment and a second compartment connected by an orifice,
   a magnetic liquid provided predominantly inside one of the first compartment or the second compartment and
   a magnet providing a magnetic force moving the magnetic liquid through the orifice from one of the first or the second compartment and into the other of the first or second compartment within a predetermined time interval.

2. A magnetic time delay indicator according to claim 1, wherein the other of the first or the second compartment not containing the magnetic liquid contains a non-magnetic liquid.

3. A magnetic time delay indicator according to claim 1, wherein the position of the first compartment and the second compartment relatively to the magnet is shiftable.

4. A magnetic time delay indicator according to claim 1, wherein the magnetic liquid is moved from one of the first or second compartment and into the other of the first or second compartment by an action performed by a user.

5. A magnetic time delay indicator according to claim 4, wherein the indicator is responsive to application of a pressure.

6. A magnetic time delay indicator according to claim 4, wherein the indicator is responsive to application of a pressure by a users finger.

7. A magnetic time delay indicator according to claim 1, wherein the magnetic liquid is moved from one of the first or second compartment and into the other of the first or second compartment by a movement of the magnetic structure.

8. A magnetic time delay indicator according to claim 7, wherein the magnetic structure is moved by a spring.

9. A magnetic time delay indicator according to claim 1, wherein the magnet is a permanent magnet.

10. An injection device incorporating a magnetic time delay indicator according to claim 1.

11. An injection device according to claim 10, wherein the indicator is responsive to application of pressure applied to an injection button.

* * * * *